(12) United States Patent  
Maître (10) Patent No.: US 7,214,060 B2
(45) Date of Patent: May 8, 2007

(54) HANDPIECE FOR DENTAL OR SURGICAL USE

(75) Inventor: Luc Maître, Epauvillers (CH)

(73) Assignee: Bien-Air Holding S.A., Bienne (CH)

( * ) Notice: Subject to any disclaimer, the term of this patent is extended or adjusted under 35 U.S.C. 154(b) by 95 days.

(21) Appl. No.: 11/046,705

(22) Filed: Feb. 1, 2005

(65) Prior Publication Data

US 2005/0181329 A1    Aug. 18, 2005

(30) Foreign Application Priority Data

Feb. 17, 2004   (EP) .................................. 04003487

(51) Int. Cl.
*A61C 1/14*   (2006.01)
*A61C 3/00*   (2006.01)

(52) U.S. Cl. ...................... 433/129; 433/128; 433/127; 433/114

(58) Field of Classification Search ......... 433/114–131
See application file for complete search history.

(56) References Cited

U.S. PATENT DOCUMENTS 3,631,597 A    1/1972  Lieb et al.
3,893,242 A *  7/1975  Lieb et al. ..................... 433/29
3,902,248 A    9/1975  Bareth
4,260,381 A    4/1981  Eibofner et al.
5,688,122 A    11/1997 Teufelberger et al.

FOREIGN PATENT DOCUMENTS

FR    1 191 869       2/1974
FR    2 723 306 A1    2/1996

* cited by examiner

*Primary Examiner*—Eduardo C. Robert
*Assistant Examiner*—Candice C. Stokes
(74) *Attorney, Agent, or Firm*—Griffin & Szipl, P.C.

(57) ABSTRACT

At the front, a handpiece (1) has a clamp (10) fitted to tightly grip the shank of a removable tool housed in guide holes (23, 25). The clamp has two or more levers (26) attached to an annular section (22) of the clamp by elastic joints (27), each of which has a gripping jaw (20) to grip the tool shank. On each lever, the gripping jaw (20) is located much closer to the joint (27) than to a supporting surface, on which a tightening mechanism (17) exerts a centripetal force so that the lever multiplies this force. The tightening mechanism preferably has a sliding sleeve (40) having a conical inside surface (44), which produces the force at the levers of the clamp by means of balls (45) housed in the holes of a hollow rotatable shaft (11).

13 Claims, 9 Drawing Sheets

HANDPIECE FOR DENTAL OR SURGICAL USE

This application claims priority from European Patent Application No. 04003487.8 filed Feb. 17, 2004, the entire disclosure of which is incorporated herein by reference.

BACKGROUND OF THE INVENTION

The present invention relates to a handpiece for dental or surgical use of the type comprising: a hollow shaft, which is rotatable around a longitudinal axis and mounted by bearings in a fixed tubular sheath; a clamp mounted in a front end of the hollow shaft and having a central channel intended to receive the shank of a removable tool, the clamp having axial arms arranged around said axis, each of which are provided with a gripping jaw in the central channel, and each arm being attached to an annular section of the clamp; a tightening mechanism supported by the hollow shaft and arranged to exert a centripetal force on a supporting surface of each arm of the clamp to grip the tool shank between the gripping jaws of the clamp; and a release mechanism supported at least partially by the fixed sheath and arranged to act on the tightening mechanism at least so as to loosen the clamp.

In the case of handpieces of this type the gripping jaws are usually located at an end of the clamp, which has conical outer supporting surfaces, on which an inside cone of a tubular piece engages to thus tighten the end of the clamp on the tool shank. For example, according to patent application FR 2 191 869, corresponding to U.S. Pat. No. 3,902,248, the clamp is mounted to slide in the hollow shaft, its gripping jaws and its outer supporting surfaces being located at its front end to cooperate with the front opening of the shaft, and the clamp is kept tight by a spring, which pulls axially to the rear.

In the case where the tool held by the handpiece has to withstand relatively high stresses, in particular with respect to the torque and axial forces, the grip of the clamp must be sufficiently tight. This requires a sufficiently high axial force of the tightening spring as well as high frictional forces on the conical surfaces, which convert this axial force into radial gripping forces. The release mechanism must be able to overcome these forces by applying a sufficient axial pressure on the sliding member biased by the tightening spring. This axial pressure is then transferred to the structure of the handpiece through at least one of the bearings supporting the rotatable shaft. Most of the time, as in the construction according to patent publication FR 2 191 869, this pressure is exerted forwards and thus stresses the bearings in the opposite direction to the axial stresses which the tool is subjected to. That is to say that the bearings must be designed to withstand axial stresses in both directions.

Moreover, a relatively strong tightening spring has a relatively high weight and this constitutes a particular disadvantage for a piece, which rotates very quickly and the centring of which cannot generally be assured with precision. The resulting vibrations increase with the weight of this spring.

Patent application FR 2 723 306, corresponding to U.S. Pat. No. 5,688,122, describes a device for gripping a dental tool in a head of an angle handpiece, comprising a clamp with elastic arms formed by cut-outs in a bushing also serving as a guide tube for the tool shank. In the resting position, the gripping jaws located on the arms of the clamp are at a distance from the axis that is smaller than the radius of the tool shank in such a way that this is then gripped solely by the elasticity of the arms. This device does not require an axial tightening spring, but the centrifugal force, however, tends to release the clamp.

SUMMARY OF THE INVENTION

The present invention aims to avoid the above-mentioned disadvantages of the prior art on the basis of an arrangement, which ensures a strong grip at the level of the gripping jaws of the clamp, while restricting the axial forces affecting the tightening and release mechanisms. An additional aim of the invention is to simplify the layout of the bearing arrangements of the handpiece, in particular by reducing the axial stresses on at least one of them.

On this basis, a handpiece of the type indicated in the above introduction is provided, characterised in that each arm of the clamp comprises a lever, a first end of which is attached to the annular section by a joint and said supporting surface of which is axially spaced from this joint, the gripping jaw being located axially closer to the joint than the supporting surface.

Thus, by the action of the lever the gripping force of each gripping jaw is more than double the centripetal force applied to the supporting surface by the tightening mechanism, and in practice the lever arm ratio can easily increase to ten or more, since the tightening movement at the level of the gripping jaws can be very small.

The tightening mechanism can have a slider, which is mounted in the hollow shaft and is provided with a concave conical surface in the area of the clamp and is biased axially by a spring, which presses its conical surface against said supporting surfaces to keep the clamp tightened. If the inclination of the supporting surfaces in relation to the axis is low, the effect of the force of the spring on each lever of the clamp is further multiplied.

However, according to a preferred embodiment, the tightening mechanism has a sliding sleeve mounted around the hollow shaft and for each lever of the clamp has a transmission element disposed in a radial hole of the hollow shaft between said supporting surface of the lever and an internal cam surface of the sliding sleeve, the cam surface having an axially inclined surface such as a conical surface. This sliding sleeve can be biased in the gripping direction by a relatively weak spring. In a particularly advantageous variant, a recess forming a notch, which holds the sliding sleeve in place by the elasticity of the levers of the clamp, can be provided in the cam surface, and this enables the usual tightening spring to be omitted. Consequently, the release action no longer has to overcome the axial pressure resulting from this spring.

Other features and advantages of the present invention may be seen from the following description of various embodiments presented by non-restrictive example with reference to the attached drawings.

DETAILED DESCRIPTION OF EMBODIMENTS OF THE INVENTION

Figure 1:
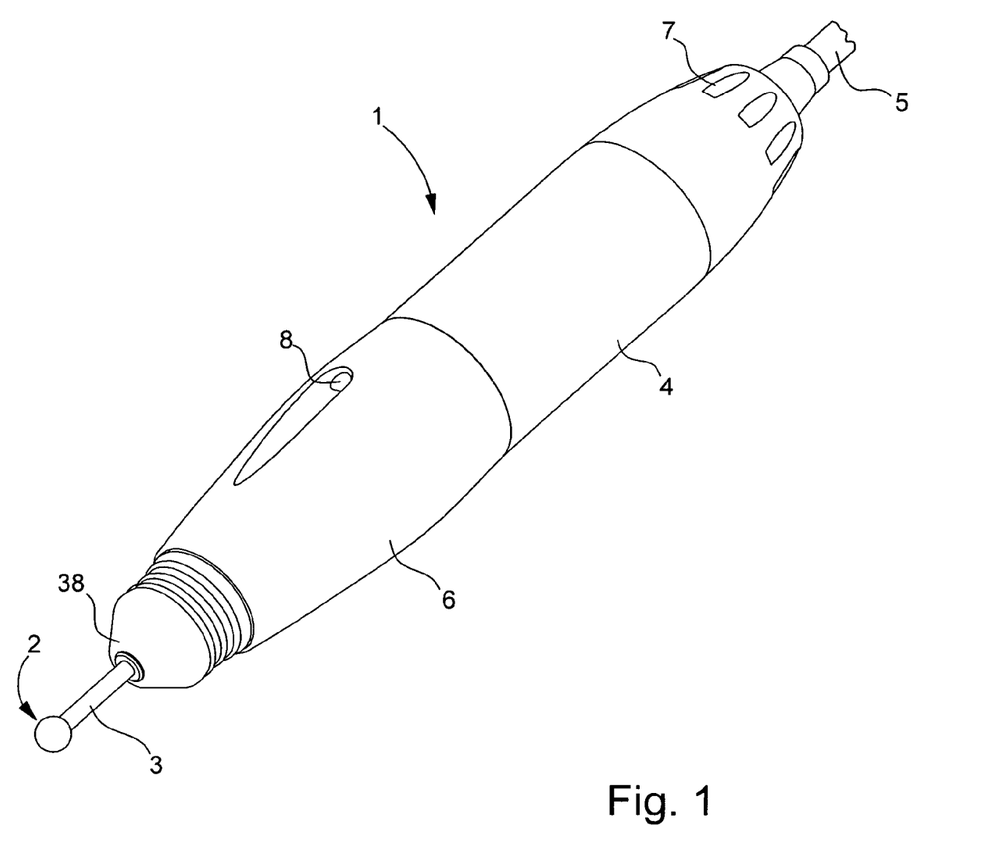
FIG. 1 is a schematic perspective view of a handpiece according to the invention.

FIG. 1 shows a handpiece 1 for dental or surgical use, in which various embodiments of the invention may be seen, which will be described further below. The handpiece is fitted with a removable rotatable tool 2 with a cylindrical shank 3, which is gripped in a rotatable clamp of handpiece 1. This contains a motor, i.e. an electric motor, to cause tool 2 to rotate at high speed. The motor is housed in the main body 4 of the handpiece and is supplied with power and controlled from an external unit via an electric cable 5 connected to the rear of the handpiece. The operator controls the tightening and release of the clamp by causing a sleeve 6 rotatably mounted on body 4 to rotate in one direction or the other. References 7 and 8 refer to vents. Such an instrument finds application in particular in dental practices, dental laboratories and in microsurgical techniques. In the examples shown here, it is an instrument for a dental laboratory using tools having a shank with a standard diameter of 2.35 mm.

A first embodiment of a clamp 10 for gripping the tool and of the tightening and release mechanisms of this clamp shall now be described with reference to FIGS. 2 to 5. Clamp 10 is located in the front end of the handpiece inside a hollow rotatable shaft 11 coupled to shaft 12 of the electric motor 13. Shaft 11 is supported by ball bearings 14 and 15 in a sheath 16 fixed to body 4 of the handpiece, and it can thus rotate at speeds in the order to 50 000 revs/minute in the instrument shown here. However, a gripping clamp such as clamp 10 may also be used in instruments, in which the tool can rotate several hundreds of thousands revs. per minute, in particular with an air turbine drive.

Figure 2A:
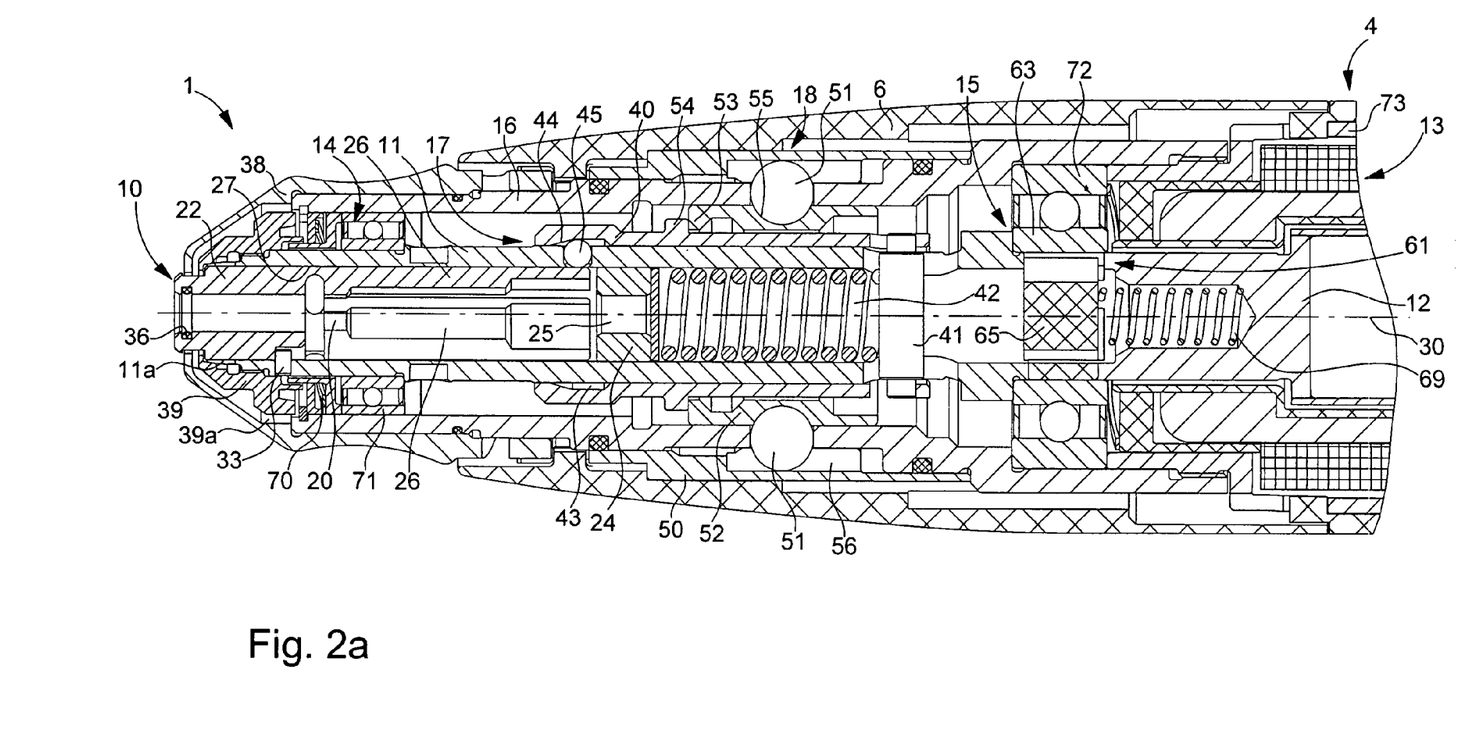
FIG. 2, divided in two sections 2(*a*) and 2(*b*), is a view in longitudinal section of a first embodiment of the handpiece according to FIG. 1, comprising a clamp connected to a ball-type tightening mechanism.
Figure 2B:
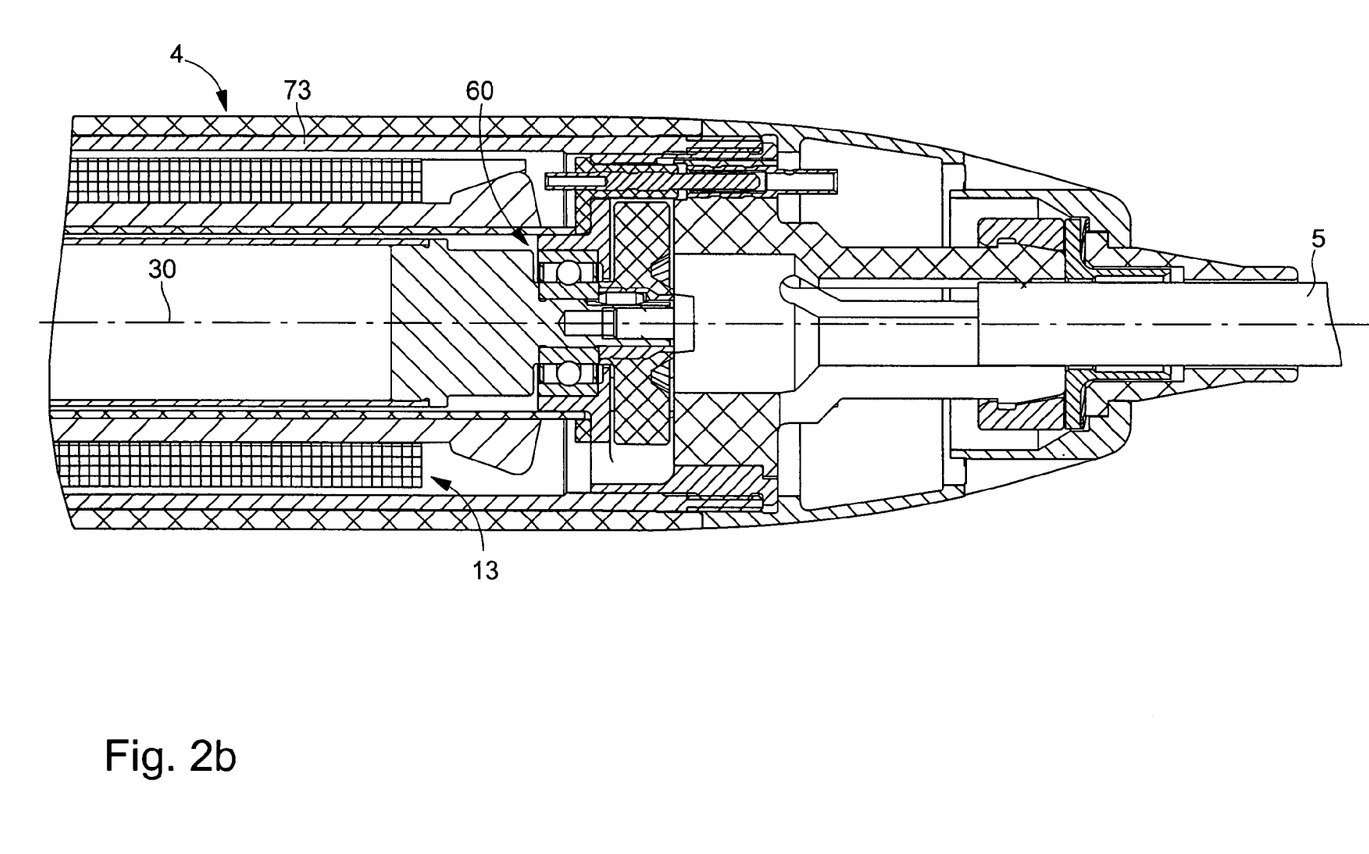

A mechanism 17 for tightening clamp 10 is mounted on shaft 11 and rotates with it. A mechanism 18 for releasing the clamp, which is controlled by the rotation of sleeve 7, is mounted on the non-rotatable sheath 16 and can act on tightening mechanism 17 in order to free the tool when the rotation has stopped. These mechanisms will be described in detail below.

Figure 3:
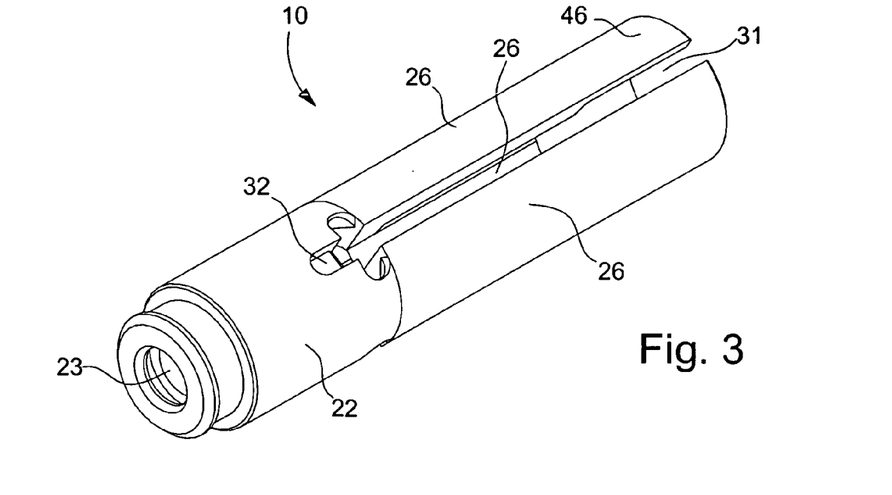
FIGS. 3 to 5 show the clamp seen in FIG. 2 in perspective, in longitudinal section and in side view respectively.
Figure 4:
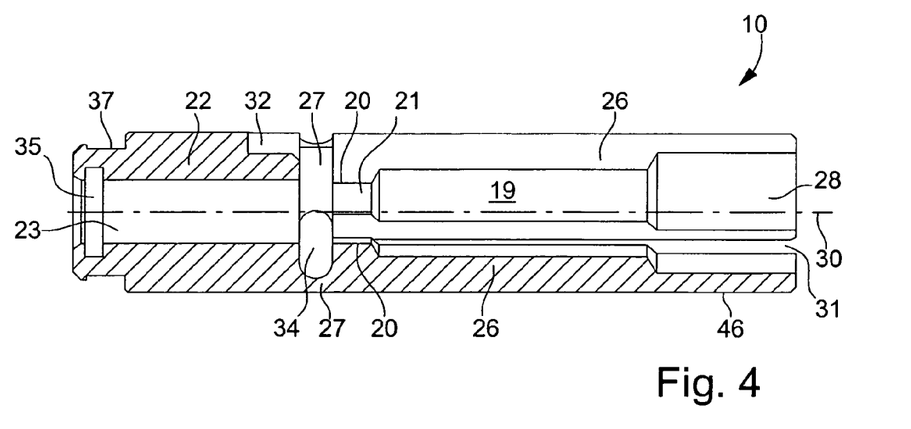
Figure 5:
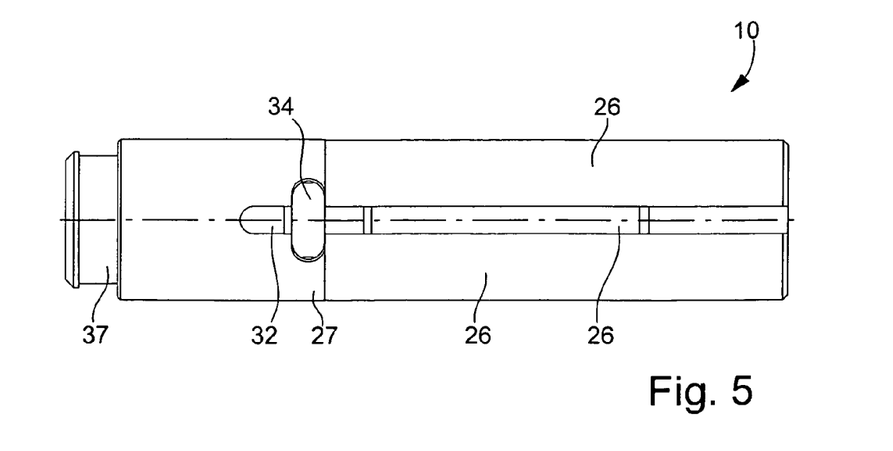

FIGS. 3 to 5 more particularly show the first embodiment of clamp 10, which in this case has three gripping jaws 20 uniformly distributed around a central channel 19 of the clamp to receive tool shank 3. Each gripping jaw 20 has a cylindrical surface portion 21 intended to engage against the tool shank.

At the front, clamp 10 has an essentially cylindrical entry tube 22 provided with an axial hole 23 calibrated to high precision in order to centre the tool as perfectly as possible.

It will be seen from FIG. 2 that a rear guide tube 24 is fixed in shaft 11 at the rear of clamp 10 and has a central hole 25 intended to guide the end of the tool shank.

Each gripping jaw 20 forms an integral part of a respective lever 26, which extends axially towards the rear from tube 22, to which it is attached by a flexible part 27 forming a joint, as it were, on which lever 26 can pivot in the direction of the axis of rotation 30 of the shaft. On each lever 26, gripping jaw 20 is located much closer to flexible part 27 than to a free end 28 of the lever, so that a radial force applied to the lever close to its end 28 produces a very high gripping force at the level of gripping jaw 20.

The clamp 10 shown in the drawings is preferably made from a single piece of metal, e.g. steel. Levers 26 are separated from one another by axial slits 31, each continuing via a slot 32 into the rear of tube 22. A pin 33, which rotatably holds clamp 10 and hollow shaft 11, engages into each slot 32. Transverse slits 34 reduce the thickness of the levers 26 at their base and thus define flexible parts 27 in three peripheral regions of the cross-section of the clamp. At the front of entry tube 22, an inner annular groove 35 is provided for an O ring 36 and an outer annular groove 37 for the lips of a fixed cap 38 and a screw 39 screwed into shaft 11 to axially hold clamp 10. Screw 39 is provided with ventilation fins 39a intended to create a slight pressure of air under cap 38 in order to prevent contaminants from entering through the slit between the cap and tube 22. In addition, screw 39 radially tightens end 11a of hollow shaft 11 against tube 22, this end being thin and divided into flexible tabs by axial slits. This ensures that clamp 10 is centred without play in the hollow shaft.

In a variant not shown here, entry tube 22 can be a separate piece that does not form part of clamp 10. The front of said clamp is then formed by a short annular section, to which levers 26 are attached by a joint. This annular section can be a separate piece from the levers, where required, but a configuration in one piece is generally preferred.

Tightening mechanism 17 has a sleeve 40, which is mounted to slide around hollow shaft 11, with which it is rotatably held by a cross bar 41 engaged in longitudinal slits of shaft 11 and sleeve 40. A compression spring 42 resting on rear guide tube 24 pushes bar 41 axially to the rear. The front end of sleeve 40 has an inside groove 43 defined at the front by a conical surface 44. Three balls 45 are housed in corresponding holes of hollow shaft 11 and have a diameter corresponding to the distance between the inside surface of shaft 11 and the base of groove 43 of sleeve 40. Each ball 45 rests on the outer surface of one of levers 26 of clamp 10 close to end 28 of the lever.

When sleeve 40 is freed from release mechanism 18, it tends to slide to the rear under the effect of the axial pressure of spring 42 so that its conical surface 44 pushes the end of each lever 26 radially inwards via the corresponding ball 45. As a result of the lever pivoting on flexible part 27, this force is transferred in multiplied form onto gripping jaw 20 of the lever and thus grips the tool shank very tightly and continuously during work. Persons skilled in the art will know that levers 26 of the clamp can be either rigid or slightly flexible in such a tightening mechanism. If they are rigid, the radial displacements of their ends are simply a little too short, and the same applies to the axial displacement of sleeve 40. In both cases, a high gripping force at the level of gripping jaws 20 is maintained continuously, even if the force of spring 42 is relatively low, as a result of the effect of the lever of the clamp and also as a result of the slight inclination of conical surface 44 in relation to axis 30. This slight inclination also means that the centrifugal force acting on levers 26 is not able to overcome the effect of spring 42. It must be noted in addition that the transfer of stresses via balls 45 is achieved with very little friction, and this also assists in maintaining a determined gripping force. However, these balls are not indispensable and they could be replaced by other transmission elements passing through shaft 11 and acting on levers 26.

Figure 6:
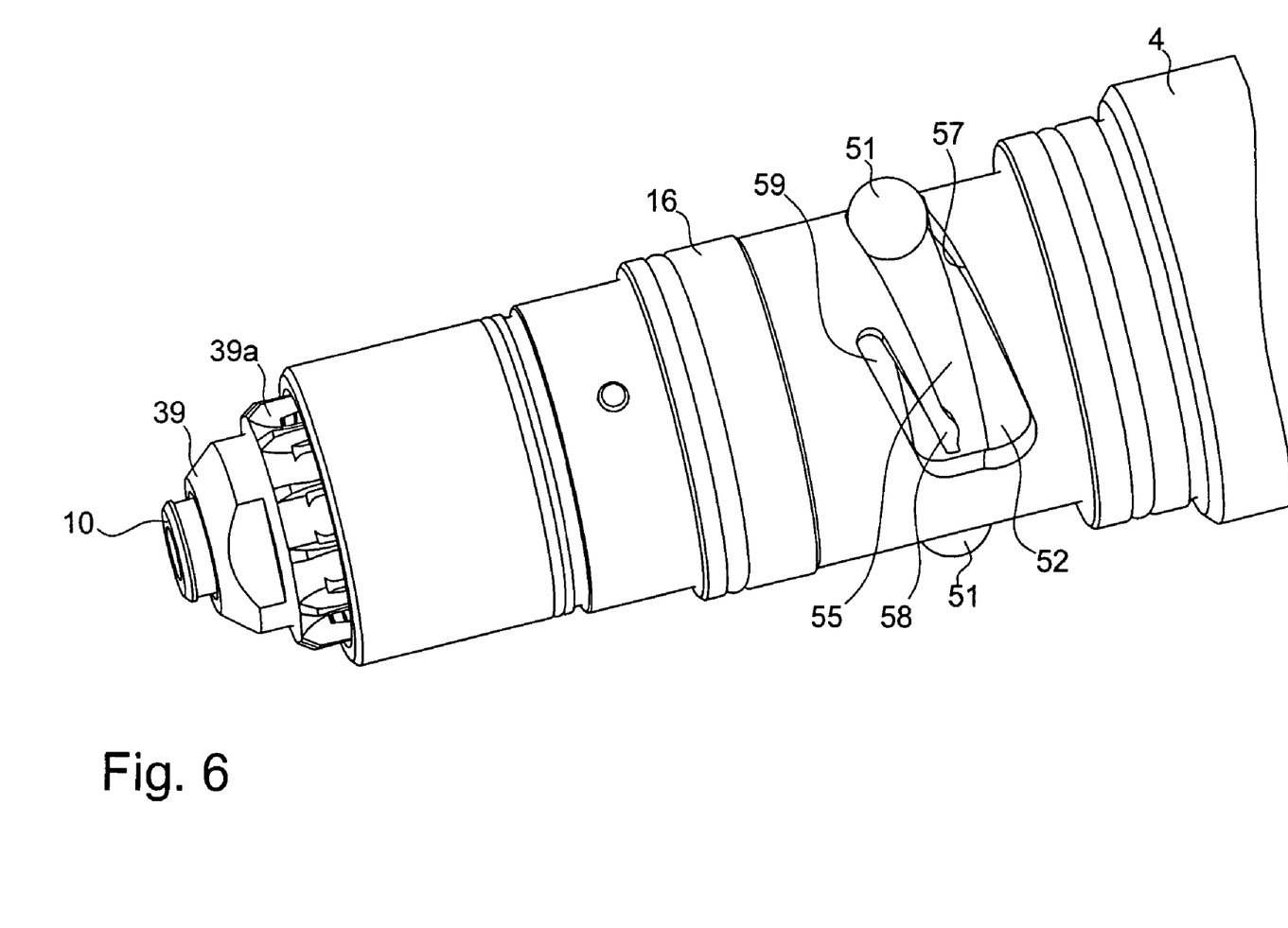
FIG. 6 is a partial perspective view of a control device for gripping the clamp.

Release mechanism 18 is designed to push sleeve 40 forwards against the force of spring 42 when the user causes control sleeve 6 to rotate on body 4 in the corresponding direction. It comprises a bushing 50 rotatably connected to control sleeve 6, one or more balls 51, in this case two balls disposed symmetrically in relation to the axis 30 of the handpiece, and a thrust collar 52 mounted to slide in sheath 16, and having at the front an inside shoulder 53 for axial support against an outer flange 54 of sleeve 40 when the latter is not rotating. Balls 51 are engaged in an annular outer groove 55 of collar 52. In addition, each ball 51 is engaged in a corresponding axial groove 56 of bushing 50 and in an inclined slit 57 (FIG. 6) of sheath 16. The course of each slit 57 is essentially helical to determine a certain axial displacement of ball 51, and its ends can be slightly bent to better define a stop position of the ball. In the preferred embodiment shown in FIG. 6, the rear end of each slit 57, corresponding to the retracted position of collar 52 and thus to a tightened state of clamp 10, is fitted with a flexible tab 58, the end of which has a protrusion, which holds ball 51 by engagement at the end of slit 57. This results in the rotatable control sleeve 6 being held elastically to prevent any inadvertent operation and indicates to the user that he/she is departing from the normal working position of the clamp. It should be noted that flexible tab 58 is simply made by milling an additional slit 59 into sheath 16.

Figure 7:
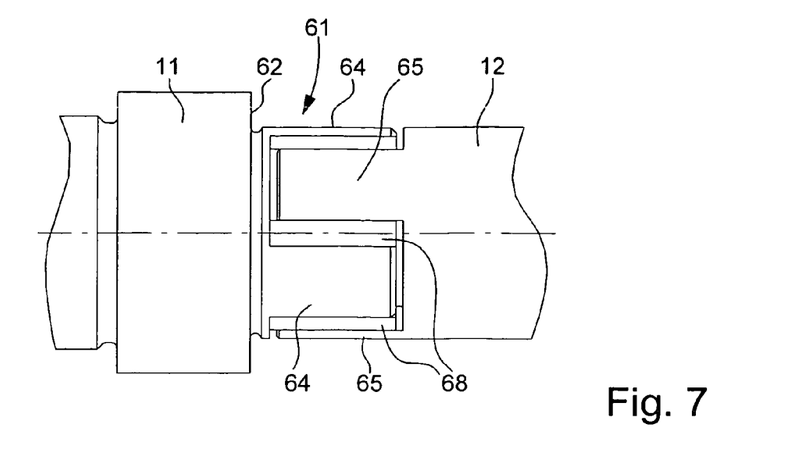
FIG. 7 is a view of the coupling between the two shafts of the handpiece.
Figure 8:
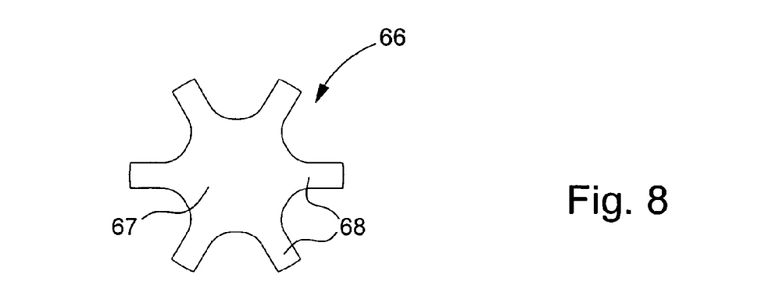
FIG. 8 shows an intermediate part of the coupling.

A remarkable aspect of the handpiece, shown in particular in FIG. 2, is the fact that the rotating part is supported by only three bearing arrangements, i.e. the front ball bearing 14, the central ball bearing 15 and a rear ball bearing 60, both of the two coaxial shafts 11 and 12 being supported by central bearing 15, inside which they are rotatably connected to one another by a positive coupling 61 shown most particularly in FIGS. 2, 7 and 8. The rear end of hollow shaft 11 has a shoulder 62, which abuts against an inner ring 63 of the bearing 15. It additionally has a set of teeth 64 inserted in ring 63, in this case three teeth distributed at 120 degrees from one another over the circumference. The front end of motor shaft 12 is inserted into the inner ring 63 of the bearing 15, preferably slidingly to be able to perform small axial displacements that can result from thermal expansions, axial play of the bearings and other tolerances. This end of shaft 12 also has teeth 65 extending axially between teeth 64 of the other shaft to ensure transmission of the torque in both directions between the two shafts. An intermediate piece 66, preferably made of synthetic material, has a cylindrical central body 67 and radial fins 68, which are interposed between adjacent teeth 64 and 65 to serve as cushioning. Moreover, intermediate piece 66 is axially prestressed against hollow shaft 11 by a compression spring 69 housed in shaft 12, the function of which will be outlined further below.

Front bearing 14 is prestressed by means of a diaphragm spring 70, which pushes an outer ring 72 of the bearing, which can slide in sheath 16, towards the rear. This axial prestress is transferred through bearing 14 and shaft 11 as far as the region of central bearing 15, where it is partly distributed over intermediate piece 66 and motor shaft 12 to an extent equal to the axial pressure of spring 69, and the rest is distributed in central bearing 15 in the form of a prestress which returns to sheath 16 via outer ring 72 of the bearing. The axial force that spring 69 exerts on shaft 12 clearly constitutes the axial prestress of rear bearing 60. As a result of the axial play of coupling 61 between the two shafts, this stress does not vary when the user exerts an axial pressure on the tool, since this pressure is completely absorbed by central bearing 15, the outer ring 72 of which is supported by the end of a tubular element 73 of the body 4 screwed into the rear end of sheath 16.

The construction described above has the same advantages as a classic construction with four bearings with respect to the absorption of axial stresses, but it is appreciably shorter and therefore enables the total length of the handpiece to be substantially reduced. This reduction in length has the great advantage of increasing the precision of handling by the operator, in particular by reducing the effect of stresses that cable 5 exerts on the rear end of the instrument.

Another particular advantage is that when adjacent ends of the two shafts 11 and 12 are supported and centred by the same ring 62, their concentricity is assured without any additional measure.

Figure 9:
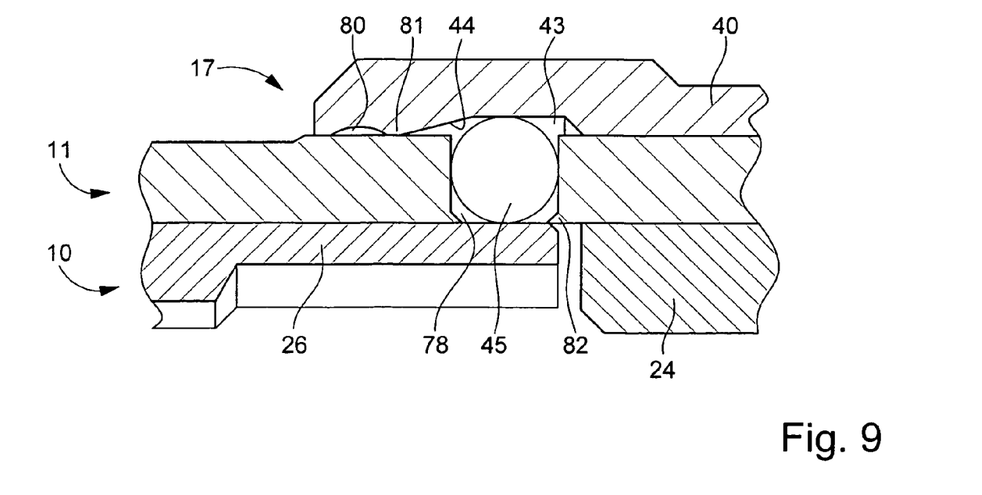
FIG. 9 is a detail view in longitudinal section showing a second embodiment resulting from a modification of the ball-type tightening mechanism shown in FIG. 2.

FIG. 9 shows a second embodiment of tightening mechanism 17, which allows appreciable simplifications over the first embodiment of the handpiece. Mechanism 17 differs from that described above mainly through the layout shown in FIG. 9 and by the omission of central spring 42 shown in FIG. 2. Release mechanism 18 thus acts as a control means for tightening and release.

In FIG. 9 one can see that the front end of sleeve 40 is modified simply by adding an annular groove 80 with a circular arc-shaped profile, this groove being separated from conical surface 44 by a short portion of cylindrical surface, which forms a radial projection 81 in relation to adjacent surfaces. In this case, each lever 26 of clamp 10 is preferably slightly flexible, which allows tightening mechanism 17 to function in the following manner.

FIG. 9 shows the release position, in which each ball 45 can run down to the bottom of groove 43 so that each lever 26 of clamp 10 can move apart until it rests against the inside surface of hollow shaft 11. Gripping jaws 20 of clamp 10 are then moved apart to the maximum distance and shank 3 of the tool can be inserted or removed.

To then tighten clamp 10, sleeve 40 is retracted by rotation of control sleeve 6, as in the preceding embodiment, but the axial displacement of sleeve 40 is greater, since it is performed until groove 80 is located on balls 45. Firstly, the movement of conical surface 44 on balls 45 pushes levers 26 towards the centre and causes them to flex when the gripping jaws of the clamp meet adequate resistance on the tool shank. As a result of this deflection, cylindrical projection 81 can pass over the balls and then groove 80 will engage on the balls and hold sliding sleeve 40 in place solely on the basis of the reaction force of levers 26 on balls 45.

The release is performed in essentially the same way as in the first embodiment, by a rotation of control sleeve 6 (FIG. 6) which causes collar 53 and the sleeve to advance to the position shown in FIG. 9.

The possibility of omitting central spring 42 shown in FIG. 2 provides quite important advantages. Firstly, the balance of the rotating part is better, since such a spring can never be perfectly centred in the hole containing it. The increase in weight also contributes to this. Secondly, the omission of this spring allows the reduction of axial forces exerted by release mechanism 18 in forward direction onto sliding sleeve 40 and consequently onto hollow shaft 11. These forces must then pass into the bearings supporting this shaft, in particular into front bearing 14, which is as small as possible and should not be subjected to too high an axial force. With the arrangement according to FIG. 9, the maximum axial force exerted on shaft 11 during release is the force necessary to cause balls 45 to exit from groove 80. Its value can be easily predetermined by the profile given to this groove.

It can be seen in FIG. 9 that a flange 82 or a series of equivalent lugs, is provided on the inside edge of cylindrical hole 78 containing ball 45 in order to hold this when clamp 10 is removed. Since this flange is not simple to produce, it may be replaced by a slight protrusion of rear tube 24 onto the outlet of hole 78 slightly shortening arms 26 of the clamp.

It should be noted that the tightening mechanism 17 described above, whether in the embodiment according to FIG. 2 or that of FIG. 9, acts only on the peripheral surfaces of clamp 10 and not on the surfaces or edges of its end. This makes various configurations of lever-type clamp possible in accordance with the principles outlined here.

If one looks at FIG. 2, one of these variants consists in retracting (to the right in the drawing) rear guide tube 24 and incorporating it into clamp 10, the two ends of levers 26 then being attached to front tube 22 and rear tube 24 respectively, the levers additionally being sufficiently thin to bend radially between the tubes under the action of balls 45. These would act on the supporting surfaces located essentially at midlength of the levers. Gripping jaws 20 could thus be located both close to front tube 22 and close to rear tube 24, thus assuring that the tool shank is held without play at two axially spaced points.

Another variant along the same lines would consist of installing two clamps like clamp 10 in shaft 11 arranged head to foot and having levers, which are narrower and spaced so that they can be positioned between the levers of the clamp without touching them. The gripping jaws of one of the clamps would be positioned at the front, while those of the other clamp would be further to the rear, thus assuring that the tool shank is held without play at two axially spaced points. The tightening mechanism could have two sets of balls 45 and two grooves 43 axially shifted in sliding sleeve 40 to act on the respective clamps.

Figure 10:
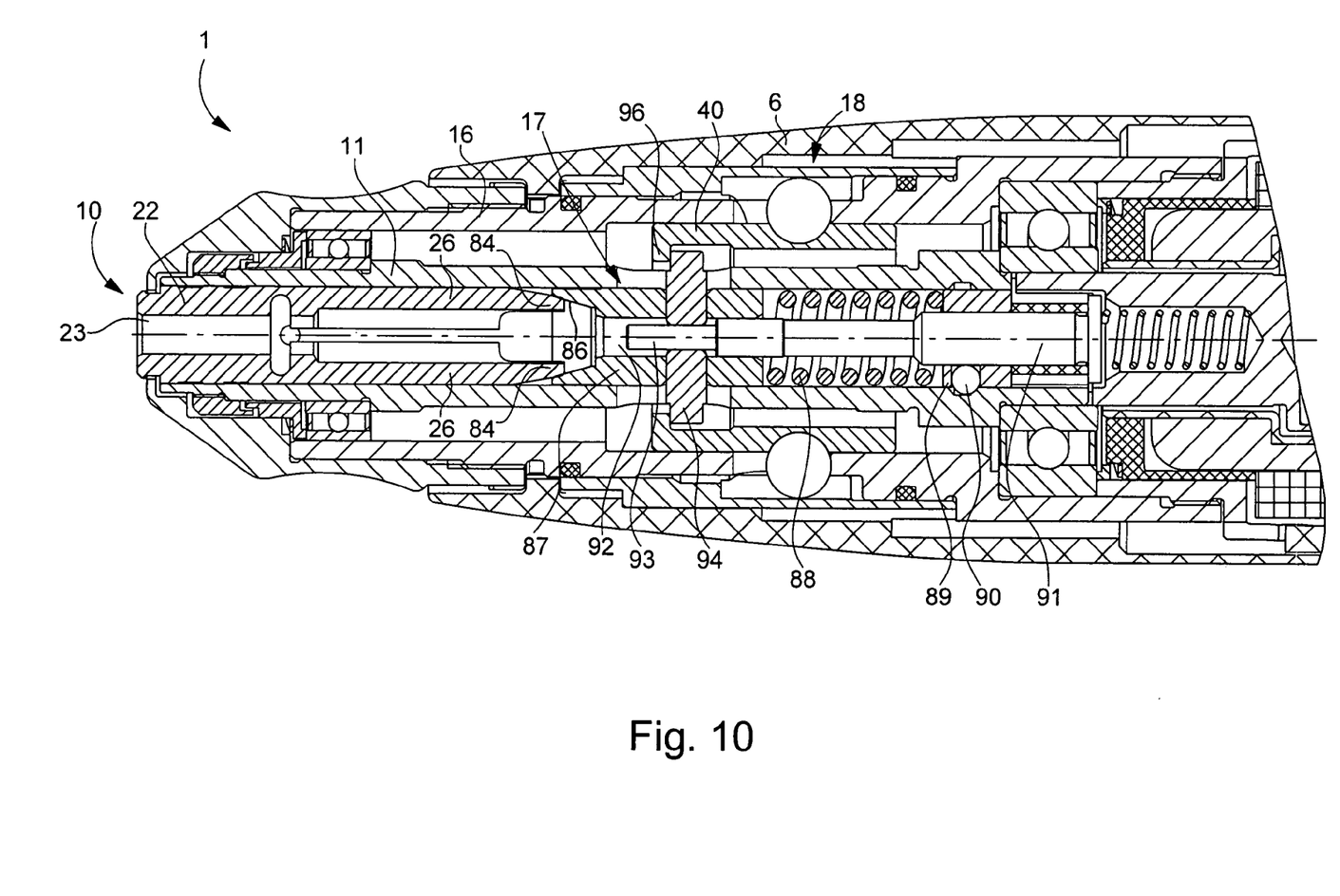
FIG. 10 is a view in partial longitudinal section of a third embodiment of the handpiece of FIG. 1 comprising a clamp connected to a cone-type tightening mechanism.
Figure 11:
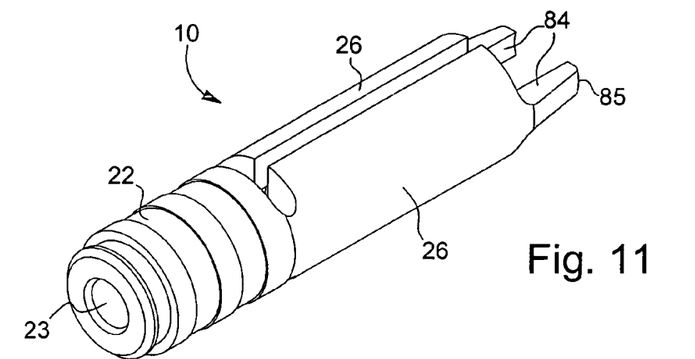
FIGS. 11 and 12 show the clamp visible in FIG. 10 in perspective and in longitudinal section respectively.
Figure 12:
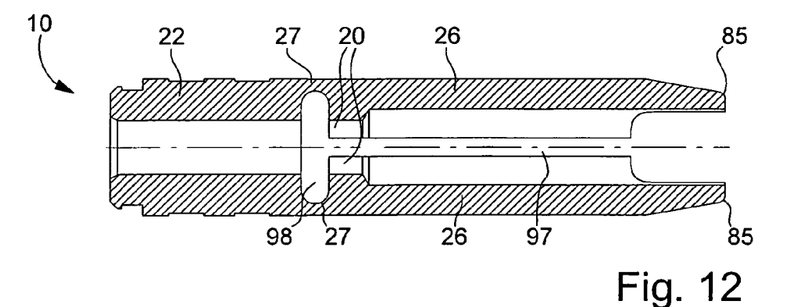

FIGS. 10 to 12 show a third embodiment of the handpiece of FIG. 1. The differences from the first embodiment lie essentially in the construction of the clamp and the tightening mechanism, and therefore only these differences will be described here using the same reference numerals for the same parts.

In this case, clamp 10 has two diametrically opposed levers 26 having free ends 84 at the rear, which are narrowed laterally and which each have an outer rounded section acting as supporting surface 85 for a concave conical surface 86 of a plunger 87 mounted in hollow shaft 11. This plunger is constantly pushed forwards by a compression spring 88 resting on a washer 89 fixed in shaft 11 by balls 90 and a plug 91. Plunger 87 has a central guide hole 92 to receive and guide the tool shank, which abuts axially against a rod 93 fixed to plug 91. This rod additionally holds a cross bar 94 on plunger 87 to allow the plunger to be pushed to the rear to detach clamp 10 by means of release mechanism 18. For this, sleeve 40 has an inner shoulder 96 at the front, which is able to rest against bar 94 when sleeve 40 is caused to retract by a rotation of control sleeve 6. Otherwise, release mechanism 18 can be the same as that described above.

As may be seen in particular in FIGS. 11 and 12, clamp 10 with two jaws described above can be made from a single piece and have an annular section acting as front guide sleeve 22 and levers 26 fitted with gripping jaws 20. All that is required are two rectilinear longitudinal slits 97, which can have a constant width, to separate the two levers 26, and a single transverse slit 98 to define the two flexible parts forming joints 27 of the levers on the periphery of the clamp.

Figure 13:
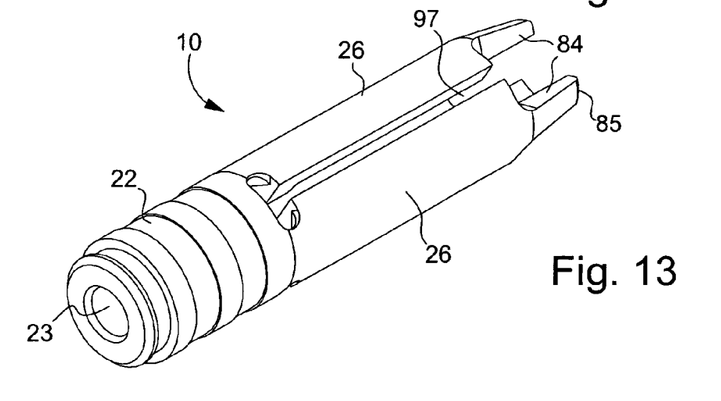
FIGS. 13 and 14 show a variant of the clamp visible in FIG. 10 in perspective and in longitudinal section respectively.
Figure 14:
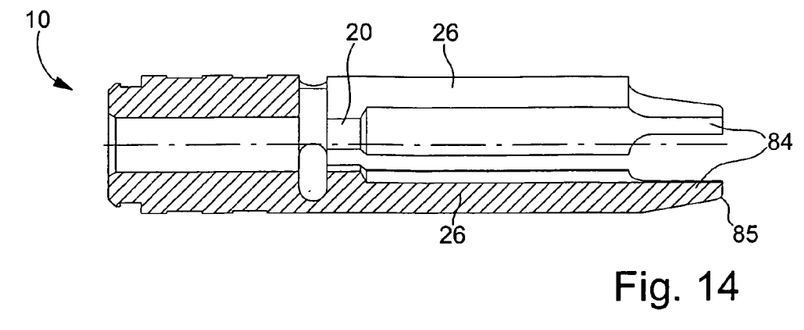

FIGS. 13 and 14 show a clamp 10 similar to that of FIGS. 10 to 12 but having three levers 26 in place of two. These levers are separated by longitudinal slits 97 spaced at 120 degrees from one another. This shows that the clamp used in the handpiece according to the invention can have any number of levers and gripping jaws greater than two.

Figure 15:
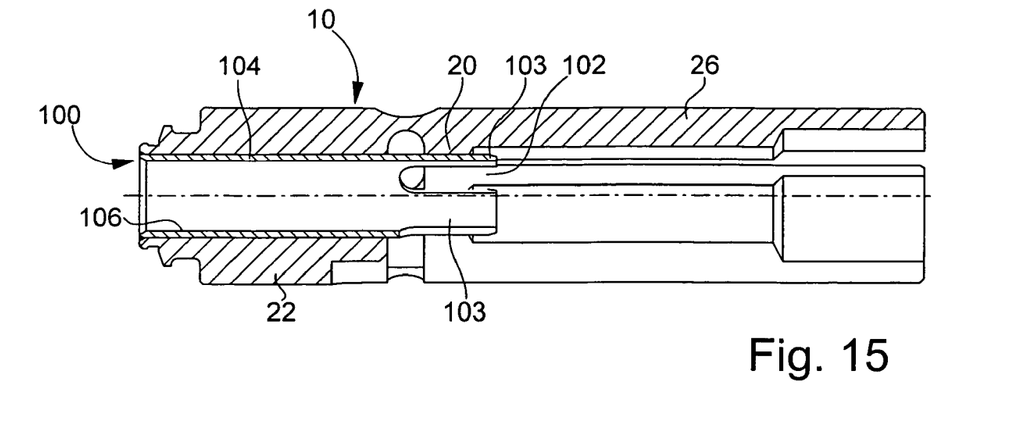
FIGS. 15 and 16 show an additional bushing, which can be combined with the clamp of the handpiece, in longitudinal section and in perspective respectively.
Figure 16:
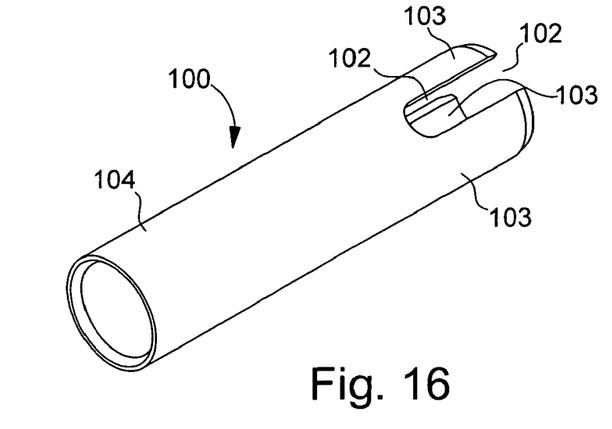

Because of the very high gripping force that the lever-type clamps described above can produce, in certain conditions, there is a risk of gripping jaws 20 damaging the tool shank or at least leaving imprints thereon. It is possible to remove this risk by interposing between gripping jaws 20 and the tool shank an additional bushing 100, an example of which is shown in FIGS. 15 and 16. This is a cylindrical tubular piece, preferably made of tempered stainless steel, which could be slotted, for example, over its entire length so that it can contract elastically under the effect of tightening of the gripping jaws. In the preferred version thereof shown here, bushing 100 has three longitudinal slits 102, which define three flexible arms 103 directed to the rear. The front portion 104 of the bushing is completely cylindrical and driven into annular section 22 of clamp 10 so that each flexible arm 103 is situated against one of gripping jaws 20 extending past the gripping surface of the gripping jaw on all sides. The flexibility of arms 103 thus prevents the edges of the gripping jaws from leaving an imprint on the tool shank. The inside surface 106 of bushing 100 is cylindrical and smooth for placement against the tool shank without marking it. Once bushing 100 is in place in clamp 10, it is advantageous to finish its inside surface. The whole assembly can then be inserted onto a centering mandrel to finish the exterior of the clamp. Such an additional bushing may be used with any of the clamps 10 described above, but the central channel of the clamp must, of course, be enlarged appropriately to correspond to the thickness of the wall of bushing 100.

What is claimed is:

1. A handpiece comprising:
   a hollow shaft, which is rotatable around a longitudinal axis and mounted by bearings in a fixed tubular sheath,
   a clamp mounted in a front end of the hollow shaft and having a central channel intended to receive a shank of a removable tool, the clamp having axial arms arranged around the longitudinal axis, each of which are provided with a gripping jaw in the central channel, and each arm being attached to an annular section of the clamp,
   said annular section located at the front end of the hollow shaft, and said arm extending axially towards the rear from said annular section,
   a tightening mechanism supported by the hollow shaft and arranged to exert a centripetal force on a supporting surface of each arm of the clamp to grip the tool shank between the gripping jaws of the clamp, and
   a release mechanism supported at least partially by the fixed sheath and arranged to act on the tightening mechanism at least so as to loosen the clamp,
   wherein each arm of the clamp comprises a lever, a first end of which is attached to the annular section by a joint and said supporting surface of which is axially spaced from the joint, the gripping jaw being located axially closer to the joint than to the supporting surface.

2. The handpiece of claim 1, wherein the annular section and the levers of the clamp are made from a single piece, said joint of each lever being an elastic joint.

3. The handpiece of claim 1, wherein the annular section comprises a guide tube for the tool shank.

4. A handpiece comprising:
a hollow shaft, which is rotatable around a longitudinal axis and mounted by bearings in a fixed tubular sheath,
a clamp mounted in a front end of the hollow shaft and having a central channel intended to receive a shank of a removable tool, the clamp having axial arms arranged around the longitudinal axis, each of which are provided with a gripping jaw in the central channel, and each arm being attached to an annular section of the clamp,
a tightening mechanism supported by the hollow shaft and arranged to exert a centripetal force on a supporting surface of each arm of the clamp to grip the tool shank between the gripping jaws of the clamp, and
a release mechanism supported at least partially by the fixed sheath and arranged to act on the tightening mechanism at least so as to loosen the clamp,
wherein each arm of the clamp comprises a lever, a first end of which is attached to the annular section by a joint and said supporting surface of which is axially spaced from the joint, the gripping jaw being located axially closer to the joint than to the supporting surface; and
wherein an additional bushing is positioned in the central channel of the clamp and has flexible parts covering the gripping jaws, in particular edges thereof, in the proximity of the tool shank.

5. A handpiece comprising:
a hollow shaft, which is rotatable around a longitudinal axis and mounted by bearings in a fixed tubular sheath,
a clamp mounted n a front end of the hollow shaft and having a central channel intended to receive a shank of a removable tool, the clamp having axial arms arranged around the longitudinal axis, each of which are provided with a gripping jaw in the central channel, and each arm being attached to an annular section of the clamp,
a tightening mechanism supported by the hollow shaft and arranged to exert a centripetal force on a supporting surface of each arm of the clamp to grip the tool shank between the gripping jaws of the clamp, and
a release mechanism supported at least partially by the fixed sheath and arranged to act on the tightening mechanism at least so as to loosen the clamp,
wherein each arm of the clamp comprises a lever, a first end of which is attached to the annular section by a joint and said supporting surface of which is axially spaced from the joint, the gripping jaw being located axially closer to the joint than to the supporting surface; and
wherein the tightening mechanism has a sliding sleeve mounted on the hollow shaft and for each lever of the clamp has a transmission element disposed in a radial hole of the hollow shaft between said supporting surface of the lever and a internal cam surface of the sliding sleeve, the cam surface having an axially inclined surface such as a conical surface.

6. The handpiece of claim 5, wherein said cam surface has a first recess provided for said inclined surface and also a second recess, which is not as deep as the first and is separated therefrom by a projecting part, and wherein the levers of the clamp are elastic so that the second recesses form a notch, which holds the sliding sleeve in place when said transmission elements are engaged in the second recesses by the elasticity of the levers.

7. The handpiece of claim 6, wherein the sliding sleeve is not biased by a spring, the release mechanism being fitted to shift it axially in both directions respectively for tightening and releasing the clamp.

8. The handpiece of claim 5, wherein said transmission elements are balls.

9. The handpiece of claim 4, wherein the clamp has a second annular section comprising a second guide tube for the tool rod, the levers of the clamp being flexible and attached to the second annular section by their second end, said supporting surface being located essentially at mid-length of each lever.

10. A handpiece comprising:
a hollow shaft, which is rotatable around a longitudinal axis and mounted by bearings in a fixed tubular sheath,
a clamp mounted in a front end of the hollow shaft and having a central channel intended to receive a shank of a removable tool, the clamp having axial arms arranged around the longitudinal axis, each of which are provided with a gripping jaw in the central channel, and each arm being attached to an annular section of the clamp,
a tightening mechanism supported by the hollow shaft and arranged to exert a centripetal force on a supporting surface of each arm of the clamp to grip the tool shank between the gripping jaws of the clamp, and
a release mechanism supported at least partially by the fixed sheath and arranged to act on the tightening mechanism at least so as to loosen the clamp,
wherein each arm of the clamp comprises a lever, a first end of which is attached to the annular section by a joint and said supporting surface of which is axially spaced from the joint, the gripping jaw being located axially closer to the joint than to the supporting surface; and
wherein on each lever of the clamp, said supporting surface is a rounded surface at the free end of the lever, and that the tightening mechanism has a slider, which is mounted in the hollow shaft and is provided with a concave conical surface in the area of the clamp and is biased axially by a spring, which presses its conical surface against said supporting surfaces to keep the clamp tight.

11. The handpiece of claim 10, wherein the slider has a guide hole intended to receive the tool shank.

12. A handpiece comprising:
a hollow shaft, which is rotatable around a longitudinal axis and mounted by bearings in a fixed tubular sheath,
a clamp mounted in a front end of the hollow shaft and having central channel intended to receive a shank of a removable tool, the clamp having axial arms arranged around the longitudinal axis, each of which are provided with a gripping jaw in the central channel, and each arm being attached to an annular section of the clamp,
a tightening mechanism supported by the hollow shaft and arranged to exert a centripetal force on a supporting surface of each arm of the clamp to grip the tool shank between the gripping jaws of the clamp, and
a release mechanism supported at least partially by the fixed sheath and arranged to act on the tightening mechanism at least so as to loosen the clamp,
wherein each arm of the clamp comprises a lever, a first end of which is attached to the annular section by a joint and said supporting surface of which is axially spaced from the joint, the gripping jaw being located axially closer to the joint than to the supporting surface; and wherein the release mechanism has a slide ring disposed in the fixed sheath and provided with an outer annular groove, a rotatable bushing, which is disposed around the fixed sheath, is connected to a manual control means and is provided with axial internal grooves, and a set of balls, each of which being engaged in one of said axial grooves, in a helical slit of the fixed sheath and in said annular groove, so that the slide ring is shifted axially by a rotation in a direction determined by the rotatable bushing and will entrain the sliding sleeve of the tightening mechanism so as to loosen the clamp.

13. The handpiece of claim 12, wherein in an inactive position of the release mechanism, on one of its edges close to its end where the ball is located, said helical slit has a flexible tab, which latches the ball in such position.

* * * * *